US012636235B2

(12) United States Patent
Rossi et al.

(10) Patent No.: US 12,636,235 B2
(45) Date of Patent: May 26, 2026

(54) CURABLE COMPOSITION FOR DENTAL IMPRESSION

(71) Applicant: DENTSPLY SIRONA Inc., York, PA (US)

(72) Inventors: Massimo Rossi, Rovigo (IT); Alberto Basso, Padua (IT); Lorenzo Galliera, Ferrara (IT)

(73) Assignee: Dentsply Sirona Inc., York, PA (US)

( * ) Notice: Subject to any disclaimer, the term of this patent is extended or adjusted under 35 U.S.C. 154(b) by 932 days.

(21) Appl. No.: 17/776,287

(22) PCT Filed: Nov. 19, 2020

(86) PCT No.: PCT/EP2020/082679
§ 371 (c)(1),
(2) Date: May 12, 2022

(87) PCT Pub. No.: WO2021/099460
PCT Pub. Date: May 27, 2021

(65) Prior Publication Data

US 2022/0401313 A1 Dec. 22, 2022

(30) Foreign Application Priority Data

Nov. 20, 2019 (EP) .................................... 19210359

(51) Int. Cl.

| | |
|---|---|
| ***A61K 6/896*** | (2020.01) |
| ***A61K 6/90*** | (2020.01) |
| ***B01J 23/14*** | (2006.01) |
| ***B01J 23/42*** | (2006.01) |

(52) U.S. Cl.
CPC ................ *A61K 6/896* (2020.01); *A61K 6/90* (2020.01); *B01J 23/14* (2013.01); *B01J 23/42* (2013.01)

(58) Field of Classification Search
CPC ........................................................ A61K 6/90
See application file for complete search history.

(56) References Cited

U.S. PATENT DOCUMENTS

| | | | | |
|---|---|---|---|---|
| 4,389,496 | A | 6/1983 | Leuesner | |
| 4,657,959 | A | 4/1987 | Bryan | |
| 5,750,589 | A * | 5/1998 | Zech | A61K 6/90 523/120 |
| 5,925,723 | A | 7/1999 | Friebe | |
| 6,218,461 | B1 | 4/2001 | Schwabe | |
| 7,592,377 | B2 | 9/2009 | Rossi | |
| 7,812,065 | B2 | 10/2010 | Bublewitz | |
| 8,466,210 | B2 | 6/2013 | Zech | |
| 2008/0319100 | A1 | 12/2008 | Bublewitz | |
| 2011/0118378 | A1 | 5/2011 | Bublewitz | |
| 2019/0240118 | A1 | 8/2019 | Angeletakis | |

FOREIGN PATENT DOCUMENTS

| | | | |
|---|---|---|---|
| CA | 3161776 | | 5/2021 |
| CN | 101938972 | A | 1/2011 |
| CN | 115038423 | | 9/2022 |
| DE | 112007000073 | A5 | 10/2008 |
| EP | 2231102 | B1 | 9/2011 |
| EP | 1976479 | B1 | 11/2011 |
| EP | 3824869 | | 5/2021 |
| EP | 4061309 | | 9/2022 |
| JP | 2010270329 | | 12/2010 |
| JP | 2011506612 | | 3/2011 |
| JP | 2023502467 | | 1/2023 |
| WO | 2009079534 | A2 | 6/2009 |
| WO | 2016143851 | | 9/2016 |
| WO | 2021099460 | | 5/2021 |

OTHER PUBLICATIONS

"European Application Serial No. 20808414.5, Noting of loss of rights pursuant to Rule 112(1) EPC mailed Mar. 26, 2024", 2 pgs.
"European Application Serial No. 19210359.6, Invitation to remedy deficiencies mailed Nov. 3, 2023", 3 pgs.
"European Application Serial No. 19210359.6, Response filed Nov. 8, 2023 to Invitation to remedy deficiencies mailed Nov. 3, 2023", 4 pgs.
"Japanese Application Serial No. 2022-529522, Notification of Reasons for Rejection mailed Jan. 7, 2025", W English Translation, 6 pgs.
"Japanese Application Serial No. 2022-529522, Response filed Apr. 1, 2025 to Notification of Reasons for Rejection mailed Jan. 7, 2025", W English Claims, 9 pgs.
"Chinese Application Serial No. 202080081041.1, Office Action mailed Sep. 27, 2023", W English Translation, 13 pgs.
"Chinese Application Serial No. 202080081041.1, Office Action mailed Apr. 30, 2024", W English Translation, 9 pgs.
International Search Report; PCT/EP2020/082679; Nov. 30, 2020 (completed); Dec. 8, 2020 (mailed).

(Continued)

*Primary Examiner* — Michael F Pepitone

(57) ABSTRACT

The present invention is related to a curable composition for dental impression comprising: a curable base composition and a surfactant system comprising a first surfactant, which is at least one compound having formula (I) and a fluorotelomer having formula (II), which works synergistically with the fluorotelomer so as to permit the composition to surprisingly have a lower contact angle; these results are reached with relatively low concentrations of biodegradable surfactants.

(I)

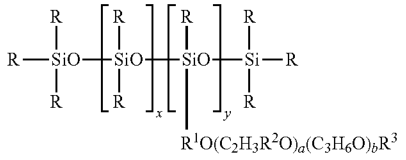

(II)

$$CF_3-(CFX)_n-(CH_2)_m-(CHOH)_p-(CYOH)$$

12 Claims, No Drawings

(56) References Cited

OTHER PUBLICATIONS

International Preliminary Report on Patentability; PCT/EP2020/082679; Nov. 30, 2020 (completed); Dec. 8, 2020 (mailed).
Written Opinion of the International Searching Authority; PCT/EP2020/082679; Nov. 30, 2020 (completed); Dec. 8, 2020 (mailed).
Liu, Jinxia et al.; Effect of Fluorotelomer Alcohol Chain Length on Aqueous Solubility and Sorption by Soils; Environ. Sci. Tecnology; 2007, vol. 41 (15); pp. 5357-5362.
Teixeua, Miguel et al.; "Complex Interfacial Behaviour of Mixtures of Fluorinated and Hydrogenated Alcohols"; Instituto Superior Tecnico, Thesis Jul. 2014.
Kissa, E, et al.; "Fluorinated Surfactant and Repellents: Second Edition, Revised and Expanded Surfactant Science Series"; vol. 97, 2001 Marcel Dekker N.Y.
Nabb, D. et al.; In Vitro Metabolism of 8-2 Fluorotelomer Alcohol: Interspecies Comparisons and Metabolic Pathway Refinement; Toxicological Sciences, vol. 100(2); 2007; pp. 333-344.
Svitova et al.; "Wetting and Interfacial Transitions in Dilute Solutions of Trisiloxane Surfactants"; Institute of Physical Chemistry, Russian Academy of Sciences, Moscow, Russia, Dow Corning Corp., Midland, Michigan, 48686, and University of Bayreuth, Bayreuth, Germany, 1998, 14, 5023-5031.
Kovalchuk et al.; "Fluror vs Hydrocarbon surfactants: why do they differ in wetting performance?"; Advance in Colloid and Interface Science; vol. 210; pp. 65-71.
Chinese Office Action dated Sep. 27, 2023 (English Translation).

* cited by examiner

CURABLE COMPOSITION FOR DENTAL IMPRESSION

CROSS-REFERENCE TO RELATED APPLICATION

This application claims the benefit of priority to PCT Application Serial No. PCT/EP2020/082679 entitled "CURABLE COMPOSITION FOR DENTAL IMPRESSION," filed Nov. 19, 2020, the disclosure of which is incorporated herein in its entirety by reference, which claims priority to European Patent Application No. 19210359.6.entitled "CURABLE COMPOSITION FOR DENTAL IMPRESSION," filed Nov. 20, 2019, the disclosure of which is incorporated herein in its entirety by reference.

FIELD OF THE INVENTION

The present invention relates to a curable composition for dental impression and a use thereof. The present invention also relates to a method of taking an impression.

BACKGROUND OF THE INVENTION

Room temperature vulcanizing silicone rubbers (RTV) are known as dental impression materials, especially for their mechanical performances and elastic properties. Moreover, addition silicones have a good dimensional stability after days from the impression taking.

Addition silicones impression materials are usually made by polysiloxanes vinyl terminated and cross linkers having Si—H groups into the chain: they typically react in the presence of a platinum catalyst (hydrosilylation reaction—see e.g. U.S. Pat. No. 7,592,377B2, Dental Materials and Their selection, William J. O'Brien, Quintessence Publishing Co.—ISBN-13: 978-0867154375).

Another class of impression materials are Condensation silicones impression materials that are normally made by polysiloxanes hydroxy terminated and alkoxysilanes cross linkers: they react usually in the presence of a tin catalyst (see e.g. Dental Materials and Their selection, William J. O'Brien, Quintessence Publishing Co.—ISBN-13: 978-0867154375, U.S. Pat. Nos. 4,389,496A, 5,925,723A, 6,218,461B1).

Fillers and additives are typically added both to addition and condensation silicones to improve their mechanical performances or get specific organoleptic properties. In particular, the use of surfactants is known to improve the impression material compatibility with oral tissues. The fluid materials, named extra light, light, regular or monophase, can therefore easily penetrate in the gingival sulcus with a better marginal sulcus detail reproduction. The surfactant performance into a dental impression material is evaluated with the contact angle measurement and, in particular, with the sessile drop method.

The use of modified trisiloxane polyalkyleneoxides super spreading surfactants, having the following formula:

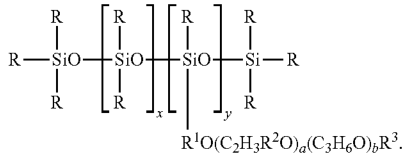

was reported in U.S. Pat. No. 4,657,959.

The modified trisiloxane polyalkyleneoxides are a powerful class of surfactants, since they have at the same time a quite high efficacy in reducing the surface tension (~20 mN/m) and, especially, a very high spread area with respect to other surfactants with a more pronounced effect in reducing the surface tension (Kovalchuk et al, Fluoro vs Hydrocarbon surfactants: why do they differ in wetting performance? Advance in Colloid and Interface Science, Volume 210 (2014), pages 65-71). The efficacy as a superspreader is lower when it is englobed in a matrix. This is caused by the lower migration capacity towards the impression material surface.

The modified trisiloxane polyalkyleneoxides cannot reach the critical wetting concentration (CWC) when they are dispersed into a complicated mixtures of ingredients. The CWC is the concentration where these surfactants become superspreader and has been determined by Svitova and others (Langmuir 1998, 14, 5023-5031).

Some compositions, containing one or more additional surfactants, have been proposed to help the modified trisiloxane polyalkyleneoxides to perform properly and reach easily the impression material surface (see e.g. EP1976479B1, U.S. Pat. No. 7,812,065, DE112007000073, EP2231102B1 ed U.S. Pat. No. 8,466,210).

US 2008/319100 A1 discloses a dental impression mass containing curable polymers selected from the group of organopolysiloxanes that crosslink by means of an addition reaction, of organopolysiloxanes that crosslink by means of a condensation reaction, of polyethers containing alkoxy silyl radicals that crosslink by means of a condensation reaction, of polyethers containing aziridino radicals that crosslink by means of an addition reaction, of polyethers containing alkenyl radicals that crosslink by means of an addition reaction, of polyethers containing ester radicals of an ethylene-unsaturated carboxylic acid that crosslink by means of a radical polymerization reaction, or of polyethers that crosslink by means of a ring-opening metathesis reaction, silicones, or rubbers, and furthermore containing at least one (poly)alkylene oxide radical as well as one silicon-containing non-ionic surfactant with a molecular mass of less than 6000 g/mol, and a non-ionic fluorosurfactant, that has at least one partially fluoridated or perfluoridated hydrocarbon radical that is connected with a (poly)alkylene oxide radical, a hydrocarbon radical, an aliphatic poly hydroxy radical, or a heterocyclic radical containing nitrogen, by way of an oxygen atom, an amino group, a keto group, a carboxylic acid ester group, a phosphoric acid ester group, a carboxylic acid amide group and/or a phosphoric acid amide group, or that has at least one partially fluoridated or perfluoridated hydrocarbon radical and at least one amino oxide radical.

US 2019/240118 A1 discloses an impression material comprising a catalyst part and a base part, the catalyst part comprises a curable organopolysiloxane polymer, a catalyst, and at least one filler; the base part comprises a curable organopolysilaxane polymer, an organopolysiloxane compound capable of crosslinking said curable organopolysiloxane polymer, at least one filler and a combination of surfactants; wherein the combination of surfactants of the base part includes fluoroaliphatic polyoxyethylene type surfactant, and a monofunctional alcohol alkoxylate type surfactant; wherein the fluoroaliphatic polyoxyethylene type surfactant is a C6 perfluorinated aliphatic chain bonded to a polyoxyethylene fragment giving an overall molecular weight range of from 400 to 800; and wherein the monofunctional alcohol alkoxylate type surfactant is of one respective formula as given in claim 1 of said document.

US 2011/118378 A1 discloses a composition containing curable polymers is disclosed selected from the group of organopolysiloxanes that crosslink by means of an addition reaction, organopolysiloxanes that crosslink by means of a condensation reaction, polyethers that contain alkoxysilyl groups and crosslink by means of a condensation reaction, polyethers that contain aziridino groups and crosslink by means of an addition reaction, polyethers that contain alkenyl groups and crosslink by means of an addition reaction, polyethers that contain ester groups of an ethylenically unsaturated carboxylic acid and crosslink by means of a radical polymerization reaction, or polyethers, silicones or rubbers that crosslink by means of a ring-opening metathesis reaction and also contain at least one nonionic and/or ionic fluorosurfactant as given in claim 1 of said document as well as also containing at least one nonionic surfactant having silicon-containing groups with a molecular weight of less than 6000 g/mol.

However, the compositions proposed so far have some drawbacks, among which the following are hereby cited: the concentration of the modified trisiloxane polyalkyleneoxides (in particular, when it is used alone) needs to be relatively high; the proposed additional surfactant/s has/have a negative environmental impact, not being biodegradable; and the contact angles obtained are not always satisfactory.

OBJECTIVE OF THE PRESENT INVENTION

It is an object of the present invention to provide a curable composition for dental impression, a use of a dental composition and a method of taking an impression, designed to at least partially overcome the aforementioned drawbacks, and which, in particular, are cheap and easy to produce and/or implement.

SUMMARY OF THE INVENTION

According to the present invention, a curable composition for dental impression, a use of a dental composition and a method of taking an impression are provided, as recited in the following independent claims and, preferably, in any one of the claims directly or indirectly depending on the independent claims. Unless explicitly specified to the contrary, the following terms have the meaning indicated below.

In the present text "aliphatic" means a non-aromatic and non-substituted (radical) hydrocarbon (unless the contrary is specified), saturated or unsaturated, linear, branched and/or cyclic. Non-limiting examples of aliphatic groups are: t-butyl, ethenyl, 1- or 2-propenyl, cyclohexyl.

In the present text, $C_x$-$C_y$ refers to a group that is meant as having from x to y carbon atoms.

In the present text "alkyl" means a saturated aliphatic (i.e., an aliphatic group without double or triple carbon-carbon bonds). Non-limiting examples of alkyls are: methyl, n-propyl, t-butyl, cyclohexyl.

In the present text "perfluorinated" compound (PFC) (or "polyfluoroalkyl" chemical) is an organofluorine compound (radical) containing only carbon-fluorine bonds and C—C bonds (no C—H bonds).

In the present text, "alkoxy" means an alkyl containing an oxygen which is bonded to two carbons.

DETAILED DESCRIPTION OF THE INVENTION

In accordance with a first aspect of the present invention, there is provided a curable composition for dental impression comprising:

a curable base composition and a surfactant system comprising a first surfactant, which has (is at least one compound having) the following formula (I)

(I)

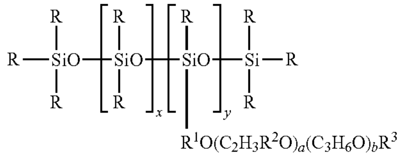

wherein R are each, independently of one another, a $C_1$-$C_4$ aliphatic; (each) $R^1$ is (independently of the others) a $C_1$-$C_6$ aliphatic; (each) $R^2$ is (independently of the others) selected from a group consisting of: H and $C_1$-$C_3$ aliphatic; (each) $R^3$ is selected (independently of the others) from a group consisting of: H and $C_1$-$C_4$ aliphatic; x is an integer from 0 to 5; y is an integer from 1 to 10; a is an integer from 1 to 30; b is an integer from 0 to 5.

Advantageously but not necessarily, R is a methyl. In addition or alternatively, (each) $R^1$ is $—C_3H_6—$. In addition or alternatively, (each) $R^2$ is an —H. In addition or alternatively, (each) $R^3$ is selected (independently of the others) from a group consisting of: —H and, a methyl; in particular, (each) $R^3$ is a methyl. In addition or alternatively, x is an integer from 0 to 1 (in particular, x is zero). In addition or alternatively, y is an integer from 1 to 5 (in particular, y is 1 or 2; more in particular, y is 1). In addition or alternatively, a is an integer from 5 to 20 (in particular, a is 6 to 8; more in particular a is 7). In addition or alternatively, b is zero.

The surfactant system further comprises a fluorotelomer, which, according to some non-limiting embodiments, has (is at least one compound having) the following formula (II):

$$CF_3—(CFX)_n—(CH_2)_m—(CHOH)_p—(CYOH) \quad \text{(II)}$$

wherein (each) X is selected (independently of the others) in the group consisting of: —F and $—CF_3$; Y is selected in the group consisting of: —H and —OH; n is an integer from 2 (in particular, to 20; more in particular, to 9); m is an integer up to 5 (in particular, from 0); p is an integer from 0 (in particular, to 2).

As regards the fluorotelomers, they have a fluorophobic effect which helps the first surfactant to get on the surface of the composition. The fluorotelomers with longer chains show the best performances, but they are solids and even insoluble in water (Effect of fluorotelomer chain length on aqueous solubility and sorption by soils, Jinxia Liu e linda S. lee, Environ. Sd. Technol., 2007, volume 41 (15), pages 5357-5362).

Long chain fluorinated alcohols tend to spontaneously form highly organized aggregates at the surface of water (Complex interfacial behaviour of mixtures of fluorinated and hydrogenated alcohols, Miguel Cabrita Teixeira, Thesis July 2014—https://fenix.tecnico.ulisboa.pt/downloadFile/281870113702050/Resumo%20alargado%20-%20Miguel%20Teixeira.pdf), but fluorinated alcohols are not fluorosurfactants as reported by E. Kissa (Fluorinated Surfactant and Repellents, Marcel Dekker N.Y.) because the hydrophilic portion of the molecule is particularly short with a consequent weak polar interaction.

For this reason, fluorotelomers are a raw material used in the manufacture of fluorotelomer-based products (In vitro metabolism of 8-2 fluorotelomer: interspecies comparisons and metabolic pathway refinement, Toxicological sciences, volume 100(2), 2007, pages 333-344). Telomerization is now the most commonly used process for manufacturing highly fluorinated substances.

Usually, in the first step a perfluoroalkyl iodide ($C_wF_{2w+1}I$) reacts with tetrafluoroethylene to get a mixture of perfluoroalkyl iodides having long perfluorinated chains, $C_wF_{2w+1}(CF_2CF_2)_kI$. In the second step, the product of the first step often reacts again with tetrafluoroethylene to get $C_wF_{2w+1}(CF_2CF_2)_kCH_2CH_2I$.

The products of the first and second step are the intermediates to prepare more "building blocks" that react to get a wide group of surfactants based on fluorotelomers and polymers (Ghislain et al., Use of Iodocompounds in Radical Polymerization, Chem. Rev. 2006, 106, 3936-3952).

The involved reactions are:

$$5F_2C{=}CF_2+IF_5+2I_2\rightarrow 5CF_3CF_2{-}I$$

$$CF_3CF_2{-}I+nnC_2F_4\rightarrow C_2F_5(C_2F_4)_{nn}{-}I$$

$$C_2F_5(C_2F_4)_{nn}{-}I+CH_2{=}CH_2\rightarrow C_2F_5(C_2F_4)_{nn}{-}CH_2{=}CH_2{-}I$$

$$C_2F_5(C_2F_4)_{nn}{-}CH_2{=}CH_2{-}I+H_2O\rightarrow C_2F_5(C_2F_4)_{nn}{-}CH_2{=}CH_2{-}OH+HI$$

It has been experimentally observed (see examples below) that the first surfactant (I) works synergistically with fluorotelomer (II) so as to permit the composition to have a surprisingly low contact angle. Please note that these results were achieved with relatively low concentration of the surfactants. In this respect, it has been supposed that the fluorotelomer increases the migration capacity of the first surfactant towards the impression material surface.

Moreover, it is important to point out that both the first and the fluorotelomer (in particular, when with short fluorinated chains) are biodegradable and therefore the composition has an environmental impact appreciably more positive with respect to the composition of the state of the art. Referring again to the fluorotelomer of formula (II), in particular, when Y is —OH, p is zero.

Advantageously but not necessarily, n is at least 3 (in particular, at least 4; more in particular, at least 5; even more in particular, at least 6). According to some non-limiting embodiments, n is up to 8 (in particular, to 7).

Advantageously but not necessarily, m is an integer from 0 to 4 (in particular, to 3; more in particular, to 2). Advantageously but not necessarily, m is at least 1. According to specific and non-limiting embodiments, m is 1. According to alternative non-limiting embodiments, m is zero.

Advantageously but not necessarily, p is an integer from 0 to 1. According to specific and non-limiting embodiments, p is 1. Alternatively (according to some advantageous but non-limiting embodiments), p is zero. According to some non-limiting embodiments, up to (no more than) two of the X are (each) —$CF_3$.

Advantageously but not necessarily, when at least one X is —$CF_3$, the fluorotelomer has (is at least one compound having) the following formula (III):

$$(CF_3)_2{-}(CF){-}(CFX)_{n-1}{-}(CH_2)_m(CHOH)_p{-}(CYOH) \quad \text{(III)}.$$

According to some non-limiting embodiments (in such cases), the fluorotelomer has (is at least one compound having) the following formula (IIIa):

$$(CF_3)_2{-}(CF){-}(CF_2)_{n-1}{-}(CF_2)_m{-}(CHOH)_p{-}(CYOH) \quad \text{(IIIa)}.$$

Advantageously but not necessarily, when two X are —$CF_3$, the fluorotelomer has (is at least one compound having) the following formula (IV):

$$(CF_3)_2{-}(CF){-}(CFX)_{n-3}{-}(CFCF_3){-}(CF_2){-}(CH_2)_m{-}(CHOH)_p{-}(CYOH) \quad \text{(IV)}.$$

According to some non-limiting embodiments (in such cases), the fluorotelomer has (is at least one compound having) the following formula (IVa):

$$(CF_3)_2{-}(CF){-}(CF_2)_{n-3}{-}(CFCF_3){-}(CF_2){-}(CH_2)_m{-}(CHOH)_p{-}(CYOH) \quad \text{(IVa)}.$$

According to some non-limiting and specific embodiments, the fluorotelomer has (is at least one compound having) a formula selected from the group consisting of (V) to (XII) (and a mixture thereof):

(V)

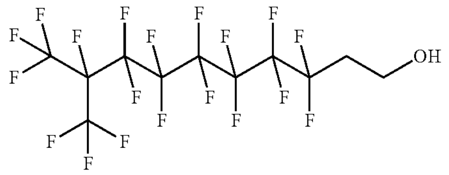

(VI)

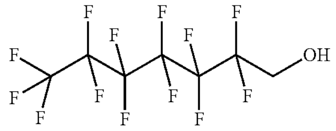

(VII)

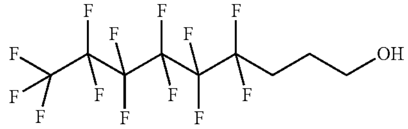

(VIII)

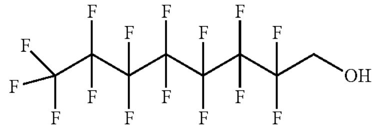

(IX)

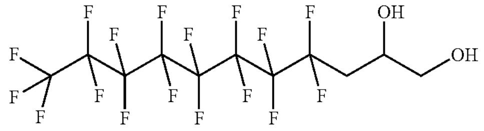

(X)

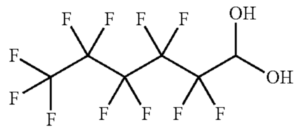

(XI)

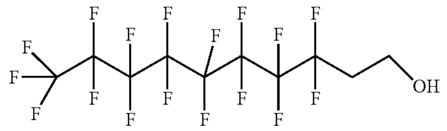

(XII)

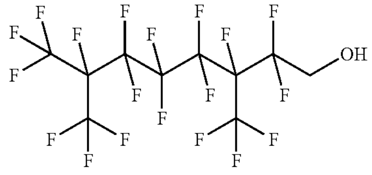

Advantageously but not necessarily, the fluorotelomer has (is at least one compound having) a formula selected from the group consisting of (V), (VII), (IX), (XI) and (XII) (and a mixture thereof). In particular, the fluorotelomer has (is at least one compound having) a formula selected from the group consisting of (IX), (XI) and (XII) (and a mixture thereof). More in particular, the fluorotelomer has (is at least one compound having) a formula selected from the group consisting of (IX) and (XI) (and a mixture thereof). In some cases, the fluorotelomer has (is at least one compound having) the formula (IX).

Advantageously but not necessarily, the curable composition comprises from approximately 0.1% (in particular, from approximately 1%; more precisely, from approximately 2%), in particular to approximately 7% (more precisely, to approximately 6%; more precisely, to approximately 5%) in weight, with respect to the total weight of the curable composition, of the first surfactant.

Advantageously but not necessarily, the curable composition comprises from approximately 0.1% (more precisely, from approximately 0.5%), in particular to approximately 7% (more precisely, to approximately 5%; even more precisely, to approximately 3%) in weight, with respect to the total weight of the curable composition, of the fluorotelomer.

Advantageously but not necessarily, the curable base composition comprises (in particular, consists of) a first component, comprising a (in particular, consisting of at least one) curable organopolysiloxane polymer; a second component, comprising a (in particular, consisting of at least one) a crosslinker compound capable of crosslinking said organopolysiloxane polymer; and (optionally) a third component, comprising (in particular, consisting of) a catalyst capable of catalysing a crosslinking reaction of the first component and the second component. According to some non-limiting embodiments, the third component is a Platinum or Tin comprising catalyst.

Advantageously but not necessarily, the curable composition comprises at least approximately 0.005% (more precisely, from approximately 0.01%), in particular up to approximately 5% (more precisely, to approximately 2%) in weight, with respect to the total weight of the curable composition, of the catalyst.

According to a first category of embodiments (in particular, when the third component comprises Platinum), the curable composition comprises at least approximately 0.005% (more precisely, from approximately 0.08%), in particular up to approximately 1% (more precisely, to approximately 0.1%) in weight, with respect to the total weight of the curable composition, of the catalyst.

According to a first category of embodiments (in particular, when the third component comprises Tin), the curable composition comprises at least approximately 0.5% (more precisely, from approximately 0.8%), in particular up to approximately 3% (more precisely, to approximately 2%) in weight, with respect to the total weight of the curable composition, of the catalyst.

According to some non-limiting embodiments, the curable base composition also comprises one or more fillers (e.g. quartz and/or fumed silica and/or precipitated silica and/or zirconium oxide and/or aluminum silicate and/or aluminum hydroxide and/or calcium silicates and/or calcium carbonate). In some cases, the curable composition comprises silicon dioxide (e.g. quartz and/or fumed silica).

In particular, the curable composition comprises from approximately 25% (in particular, from approximately 30%; more in particular, from approximately 34%) to approximately 55% (in particular, to approximately 50%) in weight, with respect to the total weight of the curable composition, of silicon dioxide.

According to some non-limiting embodiments, the curable base composition comprises (in particular, consists of) the first component, comprising a (in particular, consisting of at least one) organopolysiloxane with at least two ethylene unsaturated groups; and the second component (a crosslinker), in particular having (at least two, in particular at least three) Si—H groups (into the chain).

Organopolysiloxanes of this kind advantageously (but not necessarily) have the following formula:

$$CH_2{=}CH{-}({-}SiR^AR^BO)_w{-}SiR^AR^BCH{=}CH_2$$

where $R^A$ and $R^B$ are each, independently of one another, a substituted or un-substituted monovalent hydrocarbon (in particular aliphatic) radical. $R^A$ and $R^B$ can comprise double bonds. Examples of groups $R^A$ and $R^B$ are methyl, ethyl, phenyl, vinyl or 3,3,3-trifluoropropyl radical. Preferably but not necessarily, at least one of $R^A$ and $R^B$ is a methyl.

The value of integer w is such that the viscosity of the polymer at 23° C. is between 50 cP and 1,000,000 cP. Preferred viscosities are of 200-100,000 cP. Silicone oils with different viscosities without vinyl groups can be present as plasticizers.

In particular, the third component comprises a hydrosilylation catalyst. Said hydrosilylation catalyst can be chloroplatinic acid or a Pt siloxane complex. As an alternative said catalyst can be a metal such as Rh or Pd.

The total content of SiH in the curable base composition should be such as to ensure the complete reaction of all vinyls present in the curable base composition and, furthermore, the second component (cross-linker) can also be present in slight excess. Preferably but not necessarily, the curable base composition comprises linear or cyclic organopolysiloxanes containing a high concentration of vinyls. The presence of said linear or cyclic organopolysiloxanes containing a high concentration of vinyls has the function of adjusting the reactivity of platinum present in the Catalyst.

Other substances that can be present in the curable base composition are pigments and colorants, aromatic substances.

Another possible component is the filler which can be chosen among: extending fillers conferring filling, sliding and appearance properties; and reinforcing fillers with reinforcing function.

Whereas the first one, i.e. extending fillers, are mineral fillers with BET surface below 50 $m^2/g$ such as for instance quartz, calcium carbonate, infusorial earth, iron oxide, aluminum silicates and alumina, the second ones, i.e. reinforcing fillers, consist of fumed silica or precipitated silica with quite high BET surface and generally silanized. In some specific and non-limiting cases, the first component (the organopolysiloxane) has a viscosity from approximately 20 cP to approximately 50000 cP (in particular, from approximately 500 cP to approximately 20000 cP).

In particular, the second component (cross-linker) comprises (in particular, consists of) an organohydrogen siloxane and/or an organohydrogen polysiloxane. According to some non-limiting embodiments, the second component comprises (in particular, consists of) methylhydrogensiloxane. More precisely, the second component (in particular, the methylhydrogensiloxane) has a viscosity of 10 (in particular, from approximately 50) to approximately 200 (in particular, to approximately 70) cP (even more precisely about 60 cP). According to specific and non-limiting embodiments, the methylhydrogensiloxane has 1 to 10 mmol/g SiH content.

In particular, the third component is a Platinum comprising catalyst. In these cases, advantageously but not necessarily, the curable composition comprises at least approximately 0.005% (more precisely, from approximately 0.08%), in particular up to approximately 1% (more precisely, to approximately 0.1%) in weight, with respect to the total weight of the curable composition, of the catalyst.

According to some non-limiting embodiments, the Platinum comprising catalyst comprise (is) Karstedt catalyst.

Advantageously but not necessarily, the curable composition comprises at least approximately 35% (more precisely, at least approximately 40%), in particular up to approximately 70% (more precisely, up to approximately 65%) in weight, with respect to the total weight of the curable composition, of the first component.

According to some non-limiting embodiments, the curable composition comprises at least approximately 35% (more precisely, at least approximately 40%), in particular up to approximately 55% (more precisely, up to approximately 50%) in weight, with respect to the total weight of the curable composition, of the first component (organopolysiloxane with at least two ethylene unsaturated groups).

Advantageously but not necessarily, the curable composition comprises at least approximately 1% (more precisely, at least approximately 5%), in particular up to approximately 20% (more precisely, up to approximately 15%) in weight, with respect to the total weight of the curable composition, of the second component.

According to some non-limiting embodiments, the curable composition comprises at least approximately 3% (more precisely, at least approximately 5%), in particular up to approximately 15% (more precisely, up to approximately 10%) in weight, with respect to the total weight of the curable composition, of the second component (organohydrogen siloxane and/or organohydrogen polysiloxane).

The percentages of the different components/ingredients/additives can be varied in order to achieve the best results.

According to some non-limiting embodiments, the curable base composition comprises (in particular, consists of) a first component, comprising a (in particular, consisting of at least one) hydroxy terminated organopolysiloxane; and a second component (a cross-linker) comprising (in particular, consisting of) an alkoxysilane.

Examples of hydroxy terminated organopolysiloxanes (i.e. organopolysiloxanes that can harden by means of a condensation reaction) are known, for example, from DE 4137698 A1.

Typically, hydroxy terminated organopolysiloxanes (i.e. organopolysiloxanes that can harden by means of a condensation reaction) are compounds have the following formula (XVI)

$$HO—SiR^*_2—B1\text{-}SiR^*_2—OH \qquad (XVI)$$

wherein, R* are each, independently of one another, a $C_1$-$C_4$ aliphatic (in particular, alkyl; more in particular, a methyl); B1 stands for a radical having the formula $—O—(SiR'_2—O)_{m2}—$, wherein R' are each, independent of one another, a (in particular $C_1$-$C_6$, more in particular $C_1$-$C_4$) alkyl, alkenyl, alkinyl, cycloalkyl, aryl and/or aralkyl (which might be substituted), and m2 is an integer from 10 to 6000, preferably from 20 to 2000. According to some non-limiting examples, R' are each, independent of one another, a (in particular $C_1$-$C_6$, more in particular $C_1$-$C_4$) alkyl (such as a methyl, ethyl, n-propyl, isopropyl or n-butyl).

Typically, alkoxysilanes are compounds with one of the following formulas (XVII), (XVIII) and (XIX).

$$(R''O)_{m3}-SiR''_{3-m3}-B2-SiR''_{3-m3}-(OR'')_{m3} \qquad (XVII)$$

$$SiR''_{m4}(OR^{**})_{4-m4} \qquad (XVIII)$$

(XIX)

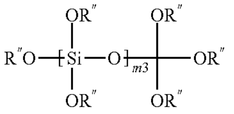

wherein R" are each, independent of one another, a (in particular $C_1$-$C_6$, more in particular $C_1$-$C_4$) alkyl, alkenyl, alkinyl, cycloalkyl, aryl and/or aralkyl (which might be substituted); R** are each, independent of one another, a (in particular $C_1$-$C_6$, more in particular $C_1$-$C_4$) alkyl, alkenyl, alkinyl, cycloalkyl, aryl and/or aralkyl (which might be substituted); m3 is an integer from 1 to 3; m4 is from 0 to 2; B2 stands for a radical having the formula $—O—(SiR^{1t}_2—O)_{m5}—$, $R^{1t}$ are each, independent of one another, a (in particular $C_1$-$C_6$, more in particular $C_1$-$C_4$) alkyl, alkenyl, alkinyl, cycloalkyl, aryl and/or aralkyl (which might be substituted); and m5 is an integer from 10 to 6000, preferably from 1 to 2000 (in particular, from 1 to 100; more in particular, from 50 to 70).

According to some non-limiting examples, R** are each, independent of one another, a (in particular $C_1$-$C_6$, more in particular $C_1$-$C_4$) alkyl (such as a methyl, ethyl, n-propyl, isopropyl or n-butyl).

According to some non-limiting examples, R" are each, independent of one another, a (in particular $C_1$-$C_6$, more in particular $C_1$-$C_4$) alkyl (such as a methyl, ethyl, n-propyl, isopropyl or n-butyl).

According to some non-limiting examples, $R^{1t}$ are each, independent of one another, a (in particular $C_1$-$C_6$, more in particular $C_1$-$C_4$) alkyl (such as a methyl, ethyl, n-propyl, isopropyl or n-butyl).

In particular, the third component is a Tin comprising catalyst. In these cases, advantageously but not necessarily, the curable composition comprises at least approximately 0.5% (more precisely, from approximately 0.8%), in particular up to approximately 3% (more precisely, to approximately 2%) in weight, with respect to the total weight of the curable composition, of the catalyst.

According to some non-limiting embodiments, the Tin comprising catalyst comprises (is) Dibutyl-Tin Dilaurate (IUPAC name [Dibutyl(dodecanoyloxy)stannyl] dodecanoate), Dibutyl-Tin Di-acetate (IUPAC name [acetyloxy(dibutyl)stannyl] acetate), Dioctyl-Tin oxide (IUPAC name Dioctyl(oxo)tin—CAS number 870-08-6) and/or Tin(II) Octanoate (IUPAC name lead(2+) octanoate). In some specific cases, the Tin comprising catalyst comprises (is) Dioctyl-Tin oxide.

Advantageously but not necessarily, the first component (hydroxy terminated organopolysiloxane) has a viscosity from approximately 500 cP to approximately 80000 cP (in particular, from 1000 cP to approximately 20000 cP).

Advantageously but not necessarily, the second component (the alkoxysilane) comprises (is) Methyltrimethoxysilane, Methyltriethoxysilane, Ethyltrimethoxysilane, Ethyltriethoxysilane, n-Propyltrimethoxysilane, Tetrakis-(butoxy-ethoxy)silane ($(CH_3—(CH_2)_3—O—(CH_2)_2—O)_4—Si$), Methyltriacethoxysilane (CAS No.: 4253-34-3).

According to some non-limiting embodiments, the curable composition comprises from approximately 1% (in particular, from approximately 2%) to approximately 5% (in particular, to approximately 4%) in weight, with respect to the total weight of the curable composition, of the second component (the alkoxysilane).

In accordance with a second aspect of the present invention, there is provided a use of the curable composition according to the first aspect of the present invention for taking a mold of at least a part of a mouth. In particular, the use comprises contacting the curable composition with at least a part of the mouth.

In accordance with a third aspect of the present invention, there is provided a method of taking an impression comprising contacting said curable composition according to the first aspect of the present invention with at least a part of a mouth. The viscosity measurements are considered to be carried out in accordance to the following. The viscosities are and were measured using a Brookfield viscometer DVII. The measurement is performed at 23° C. and 20 rpm of the spindle. An ULA spindle is and was used with a viscosity in the range 20-200 cP. The spindle SC4-21 is and was used with a viscosity in the range 500-1000 cP. The spindle SC4-29 is and was used with a viscosity in the range 2000-20000 cP. The spindle SC4-29 is and was used with a viscosity in the range 50000-100000 cP.

The viscosity measurements are and were carried out in accordance to what provided by standard DIN EN ISO 3219:1993 (in particular, on the basis of DIN 53019-1). Unless explicitly indicated to the contrary, the content of the references (articles, books, patent applications, etc.) cited in this text is herein referred to in full. In particular, the cited references are herein incorporated by reference.

Further characteristics of the present invention will be apparent from the following description of purely illustrative and non-limiting examples.

Example 1

This example discloses the procedure followed for the measurement of the contact angles (sessile drop technique). A distilled water drop was put on the hardened silicone surface, 50 μm thick, at the following environment conditions: temperature 23±1° C. and relative humidity 50±10%. A video was registered using the Kruss DSA30, filming the drop deposition. The measurement was performed after 5 and 30 seconds starting from the deposition.

The compositions tested in the following examples from 2 to 12 had the following components.

| ADDITION SILICONES COMPONENTS | Base | Catalyst |
|---|---|---|
| Polyvinylsiloxane | 31.25% | 57.29% |
| Micronized quartz (1-10 μm) | 52.08% | 42.69% |
| Methylhydrogensiloxane | 15.63% | |
| Platinum catalyst | | 0.02% |
| Pigments | 0.52% | |
| Flavors | 0.52% | |
| Surfactant | s weight phr | t weight phr |

Polyvinylsiloxane had the following viscosities: 200 cP (15% with respect to base plus catalyst, 0.28 mmol/g vinyl content), 1000 cP (5% with respect to Base plus Catalyst, 0.127 mmol/g vinyl content), 2000 cP (20% with respect to Base plus Catalyst, 0.097 mmol/g vinyl content), 20000 cP (5% with respect to base plus catalyst, 0.04 mmol/g vinyl content).

Methylhydrogensiloxane had a viscosity of 60 cP and 1.7 mmol/g as SiH content. Platinum catalyst was Karstedt catalyst (CAS Number 68478-92-2). The components mixing was performed using the following working instruction.

Firstly, the Base prepared using a vertical mixer with a cowless (sawblade impeller): pigments were dispersed in Polyvinylsiloxane for 5 minutes; thereafter, quartz and fumed silica were added and mixed for 20 minutes. During this last step, also the flavors were added and mixed for 10 minutes.

The Catalyst was prepared using a vertical mixer with a cowless (sawblade impeller): pigments were dispersed in Methylhydrogensiloxane for 5 minutes; and then quartz and fumed silica were added and mixed for 20 minutes. During the last step, the Platinum catalyst was added and mixed for 10 minutes.

Afterwards, using a disperser with a cowless (sawblade impeller) the surfactant was added to the blends described above and mixed for a total of 15 minutes.

The surfactant was added between 3 weight phr (parts per hundred rubber/resin—in weight) and 6.4 weight phr to both the blends (s and t from 3 to 6.4 weight phr). The phr is to be considered with respect to the weight of all the other components/ingredients of the composition/blend. For example, if the surfactant had 6.4 weight phr, the total weight of the composition would be 106.4 and the ratio of the weight of the surfactant with respect of the total weight of the composition would 6.4/106.4 (corresponding to about 6 wt %).

Afterwards, the Base and the Catalyst obtained after the addition of the surfactant were introduced in a 50 ml cartridge (25 ml of Base and 25 ml of Catalyst, 1:1), mixing was therefore performed using a dispenser and mixing tip for each example.

The compositions tested the examples 13 to 15 had the following components.

| CONDENSATION SILICONES COMPONENTS: | Base | Catalyst |
|---|---|---|
| Polysiloxane hydroxy terminated | 60.50% | |
| Micronized quartz (1-10 μm) | 38.50% | |
| Alkoxysilanes | | 70.00% |
| Tin catalyst | | 29.00% |
| Pigments | 0.5% | 0.5% |
| Flavours | 0.5% | 0.5% |
| Surfactant | s weight phr | t weight phr |

Polysiloxane hydroxy terminated had the following viscosities: 2000 cP (25% with respect to the base), 5000 cP (35.5% with respect to the base). Silicon dioxide was quartz and fumed silica. Alkoxysilane was Tetrakis-(butoxy-ethoxy)silane—$(CH_3—(CH_2)_3—O—(CH_2)_2—O)_4—Si$. Tin catalyst was Dioctyltin oxide. The components mixing was performed using the following working instruction.

Firstly, the Base was prepared using a vertical mixer with a cowless: pigments were dispersed in Polysiloxane hydroxy terminated in 5 minutes, then quartz and fumed silica were added and mixed for 20 minutes. During this last step, the flavors were added and mixed for 10 minutes (the last 5 minutes under vacuum).

Secondly, the Catalyst was prepared in the following way: hydrocarbons were melted in a reactor at 90° C. and mixed with pigments for a total period of 3 hours, then alkoxysilanes and flavours were added and mixed for 1 hour. Afterwards, using a disperser with a cowless, the surfactant was added to the blends described above and mixed for a total of 15 minutes. The surfactant was added with a percentage between 1 weight phr and 2.5 weight phr (s and t from 1 to 2.5 weight phr).

At the end, Base was introduced in a 140 ml tube and Catalyst in a 60 ml tube for each example. Mixing was performed by hands using a spatula and dosing Base and Catalyst with a weight ratio 10:0.32 for each example.

Example 2 (Comparative)

The surfactant was 3 weight phr Silwet L77 (Momentive™), which had the formula:

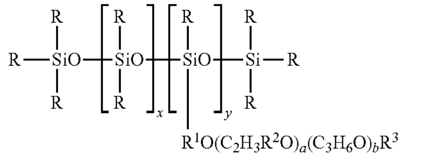

where R and $R^3$ was —$CH_3$, $R^1$ was —$C_3H_6$—, $R^2$ was hydrogen, x was 0 or 1, y was 1 or 2, a was about 7 and b was 0. The contact angle was 33.7° at 5 seconds and 15.5° at 30 seconds. This example was used as a reference for the examples from 3 to 12.

Example 3a

The surfactant was 3 weight phr Silwet L77 and 1 weight phr Formula (V)

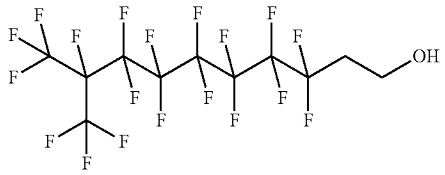
(V)

The contact angle was 6.1° at 5 seconds and 5.4° at 30 seconds. The performances were significantly better than the reference, even at 5 seconds.

Example 3b

The surfactant was 3 weight phr Silwet L77 and 1 weight phr Formula (VI)

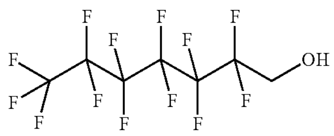
(VI)

The contact angle was 25.7° at 5 seconds and 5° at 30 seconds. The performances were better than the reference, especially at 30 seconds.

Example 4

The surfactant was 3 weight phr Silwet L77 and 1 weight phr Tridecafluorononan-1-ol (whose structure was the one shown below).

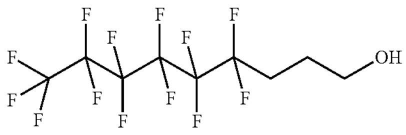
(VII)

The contact angle was 6.7° at 5 seconds and 4.8° at 30 seconds. The performances were significantly better than the reference, even at 5 seconds.

Example 5

The surfactant was 3 weight phr Silwet L77 and 1 weight phr Pentadecafluorottan-1-ol (whose structure was the one shown below).

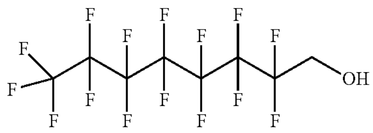
(VIII)

The contact angle was 7.2° at 5 seconds and 4.6° at 30 seconds. The performances were significantly better than the reference, even at 5 seconds.

Example 6

The surfactant was 3 weight phr Silwet L77 and 1 weight phr Formula (IX).

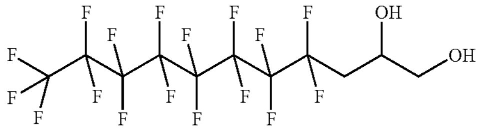
(IX)

The contact angle was 5.5° at 5 seconds and 4.4° at 30 seconds. The performances were significantly better than the reference, even at 5 seconds.

Example 7

The surfactant was 3 weight phr Silwet L77 and 1 weight phr Formula (X).

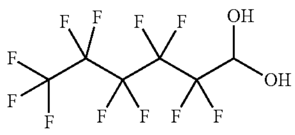
(X)

The contact angle was 28.4° at 5 seconds and 4.1° at 30 seconds. The performances were better than the reference, especially at 30 seconds.

Example 8

The surfactant was 3 weight phr Silwet L77 and 1 weight phr Formula (XI).

(XI)

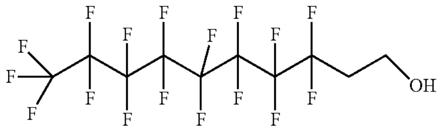

The contact angle was 4.7° at 5 seconds and 3.9° at 30 seconds. The performances were significantly better than the reference, even at 5 seconds.

Example 9

The surfactant was 3 weight phr Silwet L77 and 1 weight phr Formula (XII).

(XII)

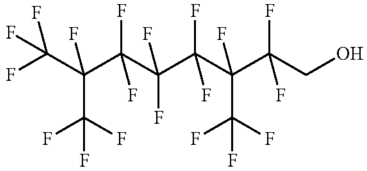

The contact angle was 6.1° at 5 seconds and 2.7° at 30 seconds. The performances were significantly better than the reference, even at 5 seconds.

Example 10 (Comparative)

The surfactant was 3 weight phr Silwet L77 and 1 weight phr FluorN 561 (Cytonix™) (whose structure contains 4 groups pendant from a matrix based on polypropylene glycol: 2 per-fluoro and 2 polyethylene glycol). The contact angle was 46° at 5 seconds and 18.4° at 30 seconds. The performances were worse than the reference (example 2).

Example 11 (Comparative)

The surfactant was 3 weight phr Silwet L77 and 1 weight phr FluorN 562 (Cytonix™) (whose structure contains 4 groups pendant from a matrix based on polypropylene glycol: 1 per-fluoro and 3 polyethylene glycol). The contact angle was 42.1° at 5 seconds and 16.4° at 30 seconds. The performances were worse than the reference (example 2).

Example 12 (Comparative)

The surfactant was 3 weight phr Silwet L77 and 1 weight phr FluorN 2900 (Cytonix) (whose structure was a perfluoroethylene with a high molecular weight, glycol terminated). The contact angle was 29.5° at 5 seconds and 13.1° at 30 seconds. The performances were not better than the reference (example 2).

Example 13 (Comparative)

The surfactant was 1 weight phr Silwet L77 (Momentive), which had the following formula:

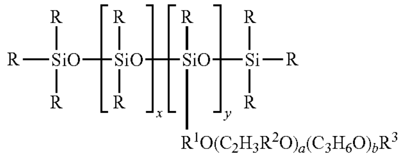

where R and $R^3$ was —$CH_3$, $R^1$ was —$C_3H_6$—, $R^2$ was hydrogen, x was 0 or 1, y was 1 or 2, a was about 7 and b was 0. The contact angle was 52.9% at 5 seconds and 35.8° at 30 seconds. This example was used as a reference for examples 14 and 15.

Example 14

The surfactant was 3 weight phr Silwet L77 and 1 weight phr Perfluorodecan-1-ol (whose structure was the one shown above (example 8). The contact angle was 26.7° at 5 seconds and 19.1° at 30 seconds. The performances were significantly better than the reference, even at 5 seconds.

Example 15

The surfactant was 3 weight phr Silwet L77 and 1 weight phr Pentadecafluorottan-1-ol (whose structure was the one shown above (example 5). The contact angle was 28.1° at 5 seconds and 20.3° at 30 seconds. The performances were significantly better than the reference, even at 5 seconds.

While the principles of the invention have been explained in relation to certain embodiments, it is to be understood that various modifications thereof will become apparent to those skilled in the art upon reading the specification.

The invention claimed is:

1. A curable composition for dental impression comprising:

a curable base composition and a surfactant system comprising a first surfactant, which is at least one compound having the following formula (I)

(I)

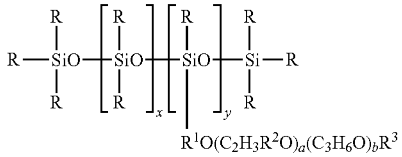

wherein R are each, independently of one another, a $C_1$-$C_4$ aliphatic; each $R^1$ is, independently of the others, a $C_1$-$C_6$ aliphatic, each $R^2$ is, independently of the others, selected from a group consisting of: H and $C_1$-$C_3$ aliphatic; each $R^3$ is selected, independently of the others, from a group consisting of: H and $C_1$-$C_4$ aliphatic; x is an integer from 0 to 5; y is an integer from 1 to 10; a is an integer from 1 to 30; b is an integer from 0 to 5;

and a fluorotelomer, which is at least one compound having the following formula (II):

$$CF_3—(CFX)_n—(CH_2)_m—(CHOH)_p—(CYZOH) \quad (II),$$

wherein each X is selected, independently of the others, in the group consisting of: —F and —$CF_3$; Y is selected in the group consisting of: —H and —OH; Z is selected in the group consisting of: —H and —OH; n is an integer from 2 to 20; m is an integer from 0 to 5; p is an integer from 0 to 2.

2. The curable composition according to claim 1, wherein each R is a methyl; each $R^1$ is —$C_3H_6$—; each $R^2$ is an H; each $R^3$ is selected, independently of the others, from a group consisting of: H and methyl; x is an integer from 0 to 1; y is an integer from 1 to 5; a is an integer from 5 to 20; b is zero;

n is an integer from 3 to 8; in is an integer from 0 to 4; p is an integer from 0 to 1.

3. The curable composition according to claim 1, wherein y is an integer from 1 to 2; a is an integer from 5 to 10;

n is an integer from 4 to 7; m is an integer from 0 to 2.

4. The curable composition according to claim 1, wherein a is an integer from 6 to 8; m is in a range of 1 to 5; up to two of the X are —$CF_3$.

5. The curable composition according to claim 1, with the proviso that, when at least one X is —$CF_3$, the fluorotelomer is at least one compound having the following formula (III):

$$(CF_3)_2—(CF)—(CFX)_{n-1}—(CH_2)_m—(CHOH)_p—(CYZOH) \quad (III).$$

6. The curable composition according to claim 1, with the proviso that, when two X are —$CF_3$, the fluorotelomer is at least one compound having the following formula (IV):

$$(CF_3)_2—(CF)—(CFX)_{n-3}—(CFCF_3)—(CF_2)—(CH_2)_m—(CHOH)_p—(CYZOH) \quad (IV).$$

7. The curable composition according to claim 1, wherein the curable base composition comprises a first component, comprising a curable organopolysiloxane polymer; a second component, comprising a crosslinker compound capable of crosslinking said organopolysiloxane polymer; a third component, comprising a catalyst capable of catalysing a cross-linking reaction of the first component and the second component.

8. The curable composition according to claim 1, wherein the curable base composition comprises a first component, comprising a organopolysiloxane with at least two ethylenically unsaturated groups; a second component, comprising an organohydrogen siloxane and/or an organopolysiloxane having Si—H groups into the chain; and, a third component that is a Platinum comprising catalyst.

9. The curable composition according to claim 1, wherein the curable base composition comprises a first component, comprising a polysiloxane hydroxy terminated; a second component comprising an alkoxysilane; and, a third component is a Tin comprising catalyst.

10. The curable composition according to claim 1, comprising from approximately 0.1% to approximately 7% in weight, with respect to the total weight of the curable composition, of the first surfactant and from approximately 0.1% to approximately 7% in weight, with respect to the total weight of the curable composition, of the fluorotelomer.

11. A curable composition comprising a curable base composition and a surfactant system comprising a first surfactant, which is at least one compound having the following formula (I)

(I)

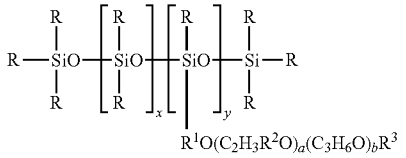

wherein R are each, independently of one another, a $C_1$-$C_4$ aliphatic; each $R^1$ is, independently of the others, a $C_1$-$C_6$ aliphatic, each $R^2$ is, independently of the others, selected from a group consisting of: H and $C_1$-$C_3$ aliphatic; each $R^3$ is selected, independently of the others, from a group consisting of: H and $C_1$-$C_4$ aliphatic; x is an integer from 0 to 5; y is an integer from 1 to 10; a is an integer from 1 to 30; b is an integer from 0 to 5;

and a fluorotelomer, which is at least one compound having the following formula (II):

$$CF_3—(CFX)_n—(CH_2)_m—(CHOH)_p—(CYZOH) \quad (II),$$

wherein each X is selected, independently of the others, in the group consisting of: —F and —$CF_3$; Y is selected in the group consisting of: —H and —OH; Z is selected in the group consisting of: —H and —OH; n is an integer from 2 to 20; m is an integer from 0 to 5; p is an integer from 0 to 2; for use in taking a mold of at least a part of a mouth.

12. A method of taking an impression comprising contacting a curable composition comprising a curable base composition and a surfactant system comprising a first surfactant, which is at least one compound having the following formula (I)

(I)

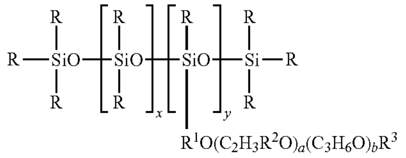

wherein R are each, independently of one another, a $C_1$-$C_4$ aliphatic; each $R^1$ is, independently of the others, a $C_1$-$C_6$ aliphatic, each $R^2$ is, independently of the others, selected from a group consisting of: H and $C_1$-$C_3$ aliphatic; each $R^3$ is selected, independently of the others, from a group consisting of: H and $C_1$-$C_4$ aliphatic; x is an integer from 0 to 5; y is an integer from 1 to 10; a is an integer from 1 to 30; b is an integer from 0 to 5;

and a fluorotelomer, which is at least one compound having the following formula (II):

$$CF_3—(CFX)_n—(CH_2)_m—(CHOH)_p—(CYZOH) \quad (II),$$

wherein each X is selected, independently of the others, in the group consisting of: —F and —$CF_3$; Y is selected in the group consisting of: —H and —OH; Z is selected in the group consisting of: —H and —OH; n is an integer from 2 to 20; m is an integer from 0 to 5; p is an integer from 0 to 2; with at least a part of a mouth.

* * * * *